(12) United States Patent
Matabe

(10) Patent No.: US 8,591,734 B2
(45) Date of Patent: Nov. 26, 2013

(54) METHOD OF SUBSTANCE SEPARATION BY SUPERCRITICAL FLUID CHROMATOGRAPHY AND VAPOR LIQUID SEPARATOR FOR USE THEREIN

(75) Inventor: Akihiro Matabe, Tokyo (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 1072 days.

(21) Appl. No.: 12/581,940

(22) Filed: Oct. 20, 2009

(65) Prior Publication Data

US 2010/0038299 A1    Feb. 18, 2010

Related U.S. Application Data

(60) Division of application No. 11/478,699, filed on Jul. 3, 2006, now Pat. No. 7,678,276, which is a continuation of application No. PCT/JP2004/019105, filed on Dec. 21, 2004.

(30) Foreign Application Priority Data

Jan. 5, 2004    (JP) ................................ 2004-000317

(51) Int. Cl.
*B01D 15/08*    (2006.01)
(52) U.S. Cl.
USPC ............. 210/198.2; 210/656; 96/101; 96/205
(58) Field of Classification Search
USPC ................ 210/635, 656, 659, 101, 137, 143, 210/198.2; 96/101, 204, 205, 209, 218
See application file for complete search history.

(56) References Cited

U.S. PATENT DOCUMENTS

| | | | |
|---|---|---|---|
| 4,478,720 | A | 10/1984 | Perrut |
| 4,724,087 | A | 2/1988 | Perrut |
| 5,180,487 | A | 1/1993 | Saito et al. |
| 6,294,088 | B1 | 9/2001 | Allington et al. |
| 6,800,316 | B1 | 10/2004 | Perrut et al. |
| 6,908,557 | B2 | 6/2005 | Chordia et al. |
| 2001/0005986 | A1 | 7/2001 | Matsubara et al. |
| 2002/0070169 | A1 | 6/2002 | Berger et al. |

(Continued)

FOREIGN PATENT DOCUMENTS

| | | |
|---|---|---|
| CN | 1192382 A | 9/1998 |
| FR | 2527934 A1 | 12/1983 |

(Continued)

OTHER PUBLICATIONS

European Search Report dated Apr. 29, 2010 for corresponding European Application No. 04807462.9.

(Continued)

*Primary Examiner* — Ernest G Therkorn
(74) *Attorney, Agent, or Firm* — Birch, Stewart, Kolasch & Birch, LLP

(57) ABSTRACT

A method comprising liquefying a gas to thereby obtain a liquefied gas; injecting a sample into a mobile phase containing a solvent and a supercritical fluid formed from the liquefied gas; passing this mobile phase through a column so that the mobile phase containing desired substance is divided into the solvent and the gas; and separating the desired substance from the solvent, wherein when the pressure of the gas divided from the mobile phase is higher than the pressure of the gas fed for formation of the liquefied gas from gas supply device, the gas divided from the mobile phase is liquefied. Further, there is provided a vapor liquid separator for use in the method.

4 Claims, 3 Drawing Sheets

(56) References Cited

U.S. PATENT DOCUMENTS

| | | |
|---|---|---|
| 2002/0070170 A1 | 6/2002 | Berger et al. |
| 2002/0139752 A1 | 10/2002 | Berger et al. |
| 2002/0144949 A1 | 10/2002 | Berger et al. |
| 2003/0019812 A1 | 1/2003 | Berger et al. |

FOREIGN PATENT DOCUMENTS

| | | |
|---|---|---|
| FR | 2584516 A1 | 1/1987 |
| FR | 2795087 A1 | 12/2000 |
| JP | 5-154303 | 6/1993 |
| JP | 5-154303 A | 6/1993 |
| JP | 5-307026 | 11/1993 |
| JP | 05-307026 A | 11/1993 |
| JP | 7-294503 | 11/1995 |
| JP | 7-294503 A | 11/1995 |

OTHER PUBLICATIONS

Pettinello et al., "Production of EPA enriched mixtures by supercritical fluid chromatography: from the laboratory scale to the pilot plant," Journal of Supercritical Fluids, vol. 19, No. 1, Nov. 15, 2000, pp. 51-60, XP-004262616.

Thienpont et al., "Studies on stereoselective separations of the "azole" antifungal drugs ketoconazole and intraconazole using HPLC and SFC on silica-based polysaccharides," Analusis, vol. 27, No. 8, Jan. 1, 1999, pp. 713-718, XP-002470692.

METHOD OF SUBSTANCE SEPARATION BY SUPERCRITICAL FLUID CHROMATOGRAPHY AND VAPOR LIQUID SEPARATOR FOR USE THEREIN

CROSS-REFERENCE TO RELATED APPLICATIONS

This application is a divisional of U.S. application Ser. No. 11/478,699 filed Jul. 3, 2006 now U.S. Pat. No. 7,678,276, which is a continuation of PCT International Application No. PCT/JP2004/019105 filed on Dec. 21, 2004, which designated the United States and upon which priority is claimed under 35 U.S.C. §120. This application also claims priority under 35 U.S.C. §119(a) on Patent Application No(s). 2004-000317 filed in Japan on Jan. 5, 2004. The entire contents of each of the above applications is hereby incorporated by reference.

TECHNICAL FIELD

The present invention relates to a method of substance separation by supercritical fluid chromatography of recovering a gas component constituting a supercritical fluid from a mobile phase containing the supercritical fluid and a solvent and recycling the gas component, and a vapor liquid separator for use in the method.

BACKGROUND ART

Each of various kinds of chromatography has been used as a method of separating a desired substance in a sample. A known example of such the chromatography is supercritical fluid chromatography using a supercritical fluid as a mobile phase. Since the supercritical fluid chromatography uses a fluid, which is referred to as a supercritical fluid and has a greater variety of properties than that of a general solvent, as a mobile phase, investigation has been conducted into the utilization of supercritical fluid chromatography for the separation, analysis, purification, and the like of various substances that have been considered to be difficult to separate.

A technique has been known as the method of substance separation by supercritical fluid chromatography, which involves: delivering a supercritical fluid supplied from a bomb by using a pump; injecting a sample into the supercritical fluid; passing the supercritical fluid into which the sample has been injected through a column; reducing the pressure of the supercritical fluid that has been passed through the column to precipitate a solute; dividing the precipitated solute and the supercritical fluid; and delivering the divided supercritical fluid to the pump to recycle the supercritical fluid (see, for example, Japanese Patent Laid-Open Publication 05-307026).

By the way, a mobile phase obtained by mixing a supercritical fluid and a solvent is used in supercritical fluid chromatography depending on the kind of a solute and the kind of a filler in some cases. The above technique does not show the use of such mobile phase, so the recycling of the supercritical fluid upon use of such mobile phase is susceptible to investigation.

DISCLOSURE OF THE INVENTION

The present invention is to provide a method of separating a substance by supercritical fluid chromatography using a mobile phase containing a supercritical fluid and a solvent, the method allowing the recycling of a gas from which the supercritical fluid is formed, and a vapor liquid separator for use in the method.

The present invention provides a method including the steps of: forming a supercritical fluid from a gas; subjecting a mobile phase that has been passed through a column to vapor liquid separation; setting the pressure of the divided gas to be higher than a pressure of a gas to be newly supplied; and placing higher priority on the use of the divided gas for the formation of the supercritical fluid than on the use of the gas to be newly supplied for the formation when the pressure of the divided gas is higher than the pressure of the gas to be newly supplied, and a vapor liquid separator to be suitably used for the method.

In other words, the present invention relates to a method of separating a substance by supercritical fluid chromatography comprising the steps of: liquefying a gas to form a liquefied gas; injecting a sample comprising a desired substance into a mobile phase comprising a supercritical fluid formed from the resultant liquefied gas and a solvent; passing the mobile phase into which the sample has been injected through a column for separating the desired substance from the sample; and dividing the mobile phase comprising the desired substance into the solvent and the gas; so that the desired substance is separated from the solvent, wherein, in the step of forming a liquefied gas, when a pressure of the gas divided from the mobile phase is higher than a pressure of a gas supplied for formation of the liquefied gas from a gas supply device, the gas divided from the mobile phase is liquefied (hereinafter, the method of the present invention is referred to "separation method" simply).

In addition, the present invention relates to a vapor liquid separator for use in a method of separating a substance by supercritical fluid chromatography of injecting a sample containing a desired substance into a mobile phase comprising a supercritical fluid and a solvent, passing the sample through a column for separating the desired substance from the sample to separate the desired substance in the sample, dividing the mobile phase that has been passed through the column into the solvent and a gas, and separating the desired substance from the solvent. The vapor liquid separator comprises: an external cylinder having ends both of which being opened; a flange portion for clogging an opening at one end of the external cylinder; an introduction portion for introducing the mobile phase into the external cylinder in a circumferential direction along an inner peripheral wall surface of the external cylinder; and an internal cylinder having ends both of which being opened and which penetrates through the flange portion to extend closer to an other end side of the external cylinder than the introduction portion.

BEST MODE FOR CARRYING OUT THE INVENTION

Figure 1:
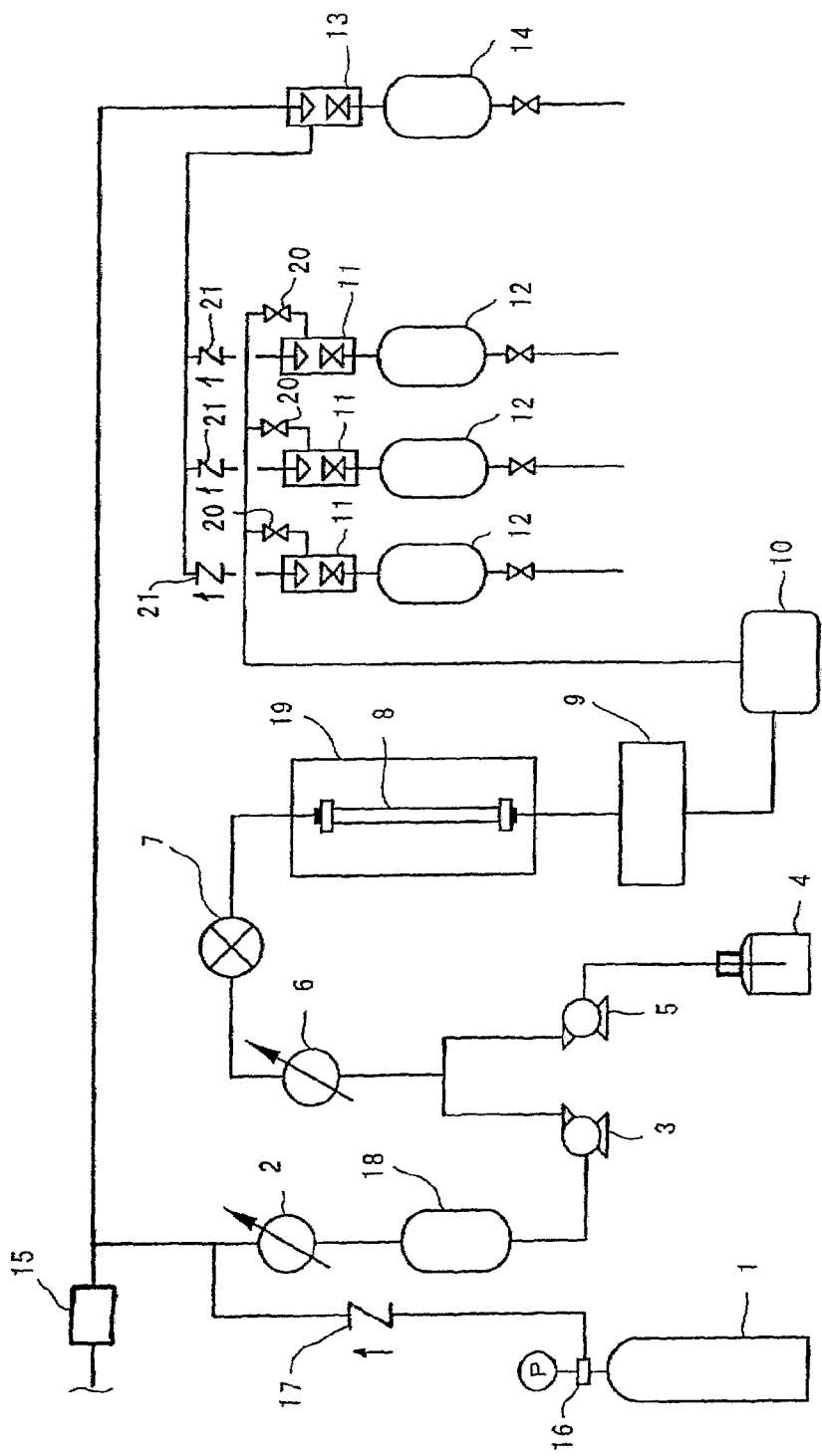
[FIG. 1] A schematic view showing the structure of an example of a supercritical fluid chromatographic fractionation apparatus for use in a separation method of the present invention.

<Method of Separating a Substance by Supercritical Chromatography>

A separation method of the present invention comprises the steps of: liquefying a gas to form a liquefied gas; injecting a sample containing a desired substance into a mobile phase containing a supercritical fluid formed from the resultant liquefied gas and a solvent; passing the mobile phase into which the sample has been injected through a column for separating the desired substance from the sample; and dividing the mobile phase containing the desired substance into the solvent and the gas.

In the step of forming a liquefied gas, the gas from which the supercritical fluid is formed is liquefied once. Such formation of the liquefied gas is performed by regulating the pressure and temperature of the gas. A pressure regulating device such as a compressor or a back pressure regulating valve can be used for regulating the pressure of the gas. Temperature regulating device such as a heat exchanger can be used for regulating the temperature of the gas.

Examples of the above-mentioned gas which can be used herein include carbon dioxide, ammonia, sulfur dioxide, hydrogen halide, nitrous oxide, hydrogen sulfide, methane, ethane, propane, butane, ethylene, propylene, halogenated hydrocarbon, and water. Of those, carbon dioxide is preferable in view of combustibility, explosivility, harmful nature to humans, ease of handling, cost efficiency, and the like.

The mobile phase in the step of injecting a sample is a mixed solvent comprising a supercritical fluid and a solvent. The supercritical fluid in the present invention is the gas having at least one or both of a pressure exceeding a critical pressure and a temperature exceeding a critical temperature. The supercritical fluid can be formed by further applying one or both of a pressure and heat to the formed liquefied gas. The mobile phase may be formed by mixing the formed supercritical fluid and the solvent, or may be formed by: mixing the liquefied gas and the solvent; applying one or both of a pressure and heat to the mixed solvent; and turning the liquefied gas in the mixed solvent into a supercritical fluid.

As performed in, for example, high performance liquid chromatography, the mixing of the liquefied gas or the supercritical fluid with the solvent can be performed by delivering each of fluids by using a metering pump at a predetermined flow rate and by mixing the fluids. The mixing ratio of the solvent, which varies depending on conditions such as a kind of a substance in the sample, is preferably about 5 to 30% by mass in the mobile phase for improving the efficiency of the separation of the desired substance. A known solvent to be selected in accordance with, for example, the kind of a substance to be separated and the kind of a filler is used as the solvent. Examples of the solvent to be used include lower alcohols such as ethanol and 2-propanol.

Known means such as an injector ordinarily used in high performance liquid chromatography can be used for injecting the sample into the mobile phase. A sample obtained by means of an ordinary method involving dissolving of a separation object into an appropriate solvent can be used as the solvent. Any one of general organic solvents or a mixed solvent of the solvents can be used as the solvent for dissolving the separation object. An injection method causing no fluctuation in pressure upon injection as described in Japanese Patent Laid-Open Publication 05-307026 mentioned above is preferably adopted in injecting the sample for improving the efficiency of the separation of the desired substance.

An appropriate column in accordance with the desired substance is used in the step of passing the mobile phase into which the sample has been injected through a column. The present invention can be suitably utilized for the separation of a substance that has been difficult to separate by any other kind of chromatography because the present invention uses a mobile phase containing a supercritical fluid. For example, when the sample contains a mixture of optical isomers and one attempts to separate one of the isomers, a column filled with a filler obtained by causing a carrier such as silica to carry a polysaccharide derivative having an optical isomer separating ability on its surface is used as the column.

An ordinary vapor liquid separator capable of dividing a solvent and a gas can be used in the step of dividing the mobile phase containing the desired substance into the solvent and the gas; however, a vapor liquid separator of the present invention to be described later is preferably used for performing high-accuracy, stable division. The desired substance can be obtained from the solvent by: releasing the divided solvent from a high-pressure condition; and adopting a known method such as vacuum concentration as required.

In the present invention, the gas divided from the mobile phase is recycled as a raw material for the liquefied gas in accordance with the pressure of the gas. That is, in the step of forming a liquefied gas, when the pressure of the gas divided from the mobile phase is higher than a pressure of a gas supplied for the formation of the liquefied gas from a gas supply device, the gas divided from the mobile phase is liquefied.

Such recycling of the divided gas can be performed by: connecting the vapor liquid separator and a device for forming the liquefied gas by using a pipe; and setting the pressure of the divided gas to be higher than the pressure of the gas from the gas supply device by using appropriate pressure regulating device. As described above, a known device such as a compressor or a back pressure regulating valve can be used as the pressure regulating device.

The pressure of the divided gas is set in accordance with not only the pressure of the gas from the gas supply device but also the solubility of the gas in the solvent from the viewpoint of the suppression of the redissolution of the divided gas into the solvent. For example, when carbon dioxide is used as the gas and an ordinary organic solvent is used as the solvent, the pressure of the divided gas is preferably set to about 1 to 10 MPa for suppressing the redissolution of the divided gas into the solvent.

The pressure of the divided gas is not particularly limited so long as it is set to be higher than the pressure of the gas from the gas supply device; however, a difference between the pressure of the divided gas and the pressure of the gas from the gas supply device is preferably 0.1 MPa or more.

The present invention may further include the step of dividing the gas from the solvent that has been divided in the dividing step. Such redividing step enables an increased amount of the gas to be recovered from the solvent, and can further increase the recovery rate of the gas.

The redividing step can be performed by reducing the pressure of a system storing the solvent. The pressure of the system storing the solvent can be continuously reduced by, for example, storing the solvent in a hermetically sealable container and gradually opening the hermetically sealable container to a lower pressure atmosphere such as a container with normal pressure or a vacuum pump.

The redividing step can be performed also by storing the solvent in a hermetically sealable container and setting the pressure of the hermetically sealable container to be lower than the pressure of the solvent before the storage. The pressure in the container may be set before the storage of the solvent, or may be set after the storage of the solvent.

Furthermore, the redividing step can be performed by connecting multiple hermetically sealable containers of the above kind in series and sequentially supplying the solvent to a container with a reduced internal pressure. The use of the multiple hermetically sealable containers as mentioned above enables an operation for dividing the gas and the solvent from the mobile phase by using the vapor liquid separator and an operation for further recovering the gas from the solvent to be performed in tandem with each other. The number of the hermetically sealable containers, which is not particularly limited, is preferably about 1 to 3 from the viewpoints of the simplicity of a facility or operation, improvement in recovery rate of the gas from the solvent, and the like.

The gas divided in the redividing step can be recycled as the liquefied gas by, for example, recovering the gas from the hermetically sealable container and compressing the recovered gas by using a compressor to liquefy the gas.

The redividing step is particularly effective in the case where a large amount of the solvent is divided in the dividing step. An example of such case is the case where a column with a large diameter is used for separating the desired substance such as industrial production. The diameter of the column in such case is preferably 10 cm or more, or more preferably 20 cm or more.

The present invention may include any other step except those described above. Examples of the other step include: the step of detecting the substance in the mobile phase that has been passed through the column; the step of supplying the mobile phase to one of multiple vapor liquid separation devices in accordance with the result of the detection of the substance in the mobile phase; and the step of purifying the divided gas.

<Vapor Liquid Separator>

A vapor liquid separator of the present invention comprises: an external cylinder having ends both of which being opened; a flange portion for clogging an opening at one end of the external cylinder; an introduction portion for introducing the mobile phase into the external cylinder in a circumferential direction along the inner peripheral wall surface of the external cylinder; and an internal cylinder having ends both of which being opened and which penetrates through the flange portion to extend closer to the other end side of the external cylinder than the introduction portion.

According to the vapor liquid separator, the internal cylinder extends closer to the other end side of the external cylinder than the introduction portion, so a gas to be discharged from the internal cylinder hardly contains a droplet of the mobile phase introduced from the introduction portion, and the concentration of the solvent or of the substance in the gas can be reduced. In addition, the external cylinder is of a cylindrical shape, so a pressure is uniformly applied to the inner peripheral wall surface and the durability of the vapor liquid separator is improved. As described above, the vapor liquid separator can recover a gas with a high purity under a high-pressure condition, so it is suitably used for a technique for recycling a recovered gas as a mobile phase in the separation of optical isomers by supercritical fluid chromatography requiring improved accuracy.

For further improving separation efficiency in vapor liquid separation in the external cylinder, the vapor liquid separator preferably further comprises: a jacket that covers the outer peripheral wall surface of the external cylinder for regulating the temperature of the external cylinder; and a mobile phase supply pipe that passes the inside of the jacket to be connected to the introduction portion for supplying the mobile phase to the introduction portion, because the temperature of the mobile phase is regulated to the temperature of the external cylinder before the mobile phase is introduced into the external cylinder.

The external cylinder is not particularly limited so long as the mobile phase introduced from the introduction portion flows from one end side of the external cylinder to the other end side along the inner peripheral wall surface in a spiral fashion. The external cylinder, which is generally of a cylindrical shape, may be a cylinder having the inner peripheral wall surface of a substantially circular sectional shape such as an elliptical shape or a polygonal shape for the purpose of, for example, causing a bias in the flow velocity of the mobile phase introduced into the external cylinder or applying an appropriate impact.

The flange portion is not particularly limited so long as it clogs an opening at one end of the external cylinder. For example, reducing unions for installing the internal cylinder and clogging the external cylinder can be suitably used as such flange portion.

The introduction portion can be formed of a nozzle or pipe for introducing the mobile phase into the external cylinder along the tangent of the inner peripheral wall surface in the sectional shape of the external cylinder. The mobile phase is ordinarily introduced in the direction parallel with the transverse direction of the external cylinder. How to provide the introduction portion is not limited to that mentioned above in the present invention. The introduction portion may be provided to be in parallel with the transverse direction of the external cylinder, or may be provided obliquely to the transverse direction.

The sectional shape of the internal cylinder is not particularly limited so long as the internal cylinder is a pipe having a diameter smaller than that of the external cylinder. The internal cylinder is constituted to extend sufficiently closer to the other end side than the introduction portion in the external cylinder from the viewpoint of prevention of a mixing of a droplet of the mobile phase into a gas in the external cylinder. The length by which the internal cylinder extends varies depending on various conditions such as conditions for introducing the mobile phase into the external cylinder, the diameter of the external cylinder, and the diameter of the internal cylinder. The internal cylinder has only to be extended up to the position at which the flow of the mobile phase introduced into the external cylinder is prevented from losing its posture so that the mobile phase propagates along the inner peripheral wall surface of the external cylinder, that is, a droplet is not generated from the inner peripheral wall surface.

An ordinary jacket for circulating a heat medium to the outside of the external cylinder can be used as the jacket. Using a hot heat medium for the heat medium to be supplied to the jacket is effective in improving the efficiency of the division of the gas. Using a refrigerant for the heat medium to be supplied to the jacket is effective in reducing the solubility of the desired substance in the solvent.

The mobile phase supply pipe is preferably provided over a wide range in the jacket from the viewpoint of regulation of the temperature of the mobile phase before vapor liquid separation to the temperature in the external cylinder in advance. For example, the mobile phase supply pipe is preferably provided in a meander shape in the jacket, or is preferably provided in a spiral fashion for the outer peripheral wall surface of the external cylinder. Such mobile phase supply pipe is preferable for suppressing a droplet due to a change in temperature of the mobile phase upon introduction of the mobile phase into the external cylinder particularly when the heat medium is a hot heat medium.

The vapor liquid separator of the present invention reduces a mixing of a droplet of the mobile phase into the gas subjected to vapor liquid separation. Accordingly, the vapor liquid separator is applicable to analyzing and separating device using such gas as a mobile phase. Applying the vapor liquid separator to a device for analyzing and separating optical isomers that may be greatly affected by mixing with impurities is effective particularly in the field of, for example, medicine.

Hereinafter, an embodiment of the present invention will be described on the basis of the drawings. First, FIG. 1 shows a supercritical fluid chromatographic fractionation apparatus for use in the separation method of the present invention.

As shown in FIG. 1, the supercritical fluid chromatographic fractionation apparatus comprises: a bomb 1 as gas supply device filled with carbon dioxide having a high pressure; a heat exchanger 2 for cooling and liquefying carbon dioxide having a high pressure; a pump 3 for delivering the liquefied gas of carbon dioxide formed in the heat exchanger 2; a pump 5 for supplying a solvent supplied from a solvent tank 4 to the liquefied gas delivered by the pump 3; a heat exchanger 6 for heating a mixed solvent of the liquefied gas and the solvent to turn the liquefied gas into a supercritical fluid; an injector 7 for injecting a sample into a mobile phase as a mixture of the formed supercritical fluid and the solvent; a column 8 for separating a desired substance in the injected sample; a detector 9 for detecting the substance in the mobile phase that has passed the column 8; a back pressure regulating valve 10 as a pressure regulating device for keeping the pressure in a system ranging from the pump 3 to the detector 9 at a predetermined pressure; multiple vapor liquid separators 11 each intended to subject the mobile phase which has passed the back pressure regulating valve 10 and of which the pressure has been regulated to vapor liquid separation; tanks 12 each intended to store a liquid that has been subjected to vapor liquid separation; a purifying device 13 for further removing a liquid from a gas that has been subjected to vapor liquid separation; a tank 14 for storing the liquid removed by the purifying device 13; and a back pressure regulating valve 15 for keeping the pressure of the gas purified by the purifying device 13 at a predetermined pressure.

The bomb 1, the heat exchanger 2, the pump 3, the heat exchanger 6, the injector 7, the column 8, the detector 9, and the back pressure regulating valve 10 are connected in series by using pipes. The vapor liquid separators 11 are connected by using pipes in parallel with the back pressure regulating valve 10 and the purifying device 13. The purifying device 13 and the back pressure regulating valve 15 are connected by using a pipe. The secondary side (side opposite to the purifying device 13) of the back pressure regulating valve 15 is connected to a pipe for discharging a gas to the outside of the system. The pipe for connecting the purifying device 13 and the back pressure regulating valve 15 bifurcates in midstream, and the bifurcated pipe is connected to the pipe on the upstream side of the heat exchanger 2. In addition, the solvent tank 4 and the pump 5 are connected by using a pipe. The pump 5 is connected to a pipe for connecting the pump 3 and the heat exchanger 6 by using a pipe. Each of the vapor liquid separators 11 and each of the tanks 12 are connected by using a pipe. The purifying device 13 and the tank 14 are connected by using a pipe.

A pressure regulating valve 16 for releasing carbon dioxide from the bomb 1 at a predetermined pressure and a check valve 17 for preventing the back flow of a gas from the side of the heat exchanger 2 to the side of the pump 1 are provided between the bomb 1 and the heat exchanger 2. A buffer tank 18 for receiving the liquefied gas formed in the heat exchanger 2 is provided between the heat exchanger 2 and the pump 3. The column 8 is stored in a column oven 19 for regulating the temperature in the column 8 to be a predetermined temperature.

A valve 20 corresponding to each of the vapor liquid separators 11 is provided between the back pressure regulating valve 10 and each of the vapor liquid separators 11 in such a manner that the destination of the mobile phase supplied from the back pressure regulating valve 10 can be selected. A check valve 21 for preventing the back flow of a gas from the side of the purifying device 13 to each of the vapor liquid separators 11 is provided between each of the vapor liquid separators 11 and the purifying device 13 in correspondence with each of the vapor liquid separators 11.

Each of the pumps 3 and 5 is a pump capable of delivering a constant amount of a liquid. The back pressure regulating valve 10 is a valve that opens or closes to let the mobile phase having a pressure equal to or higher than a predetermined pressure (for example, 20 MPa) escape to the side of the back pressure regulating valve 10 close to each of the vapor liquid separators 11, that is, the secondary side of the back pressure regulating valve 10 in such a manner that the pressure of the system on the side of the back pressure regulating valve 10 close to the column 8, that is, the primary side of the back pressure regulating valve 10 is kept at the predetermined pressure. In addition, the back pressure regulating valve 15 is a valve that opens or closes to let a gas having a pressure equal to or higher than a predetermined pressure (for example, 9.5 MPa) escape to the side of the back pressure regulating valve 15 close to the pipe for discharging, that is, the secondary side of the back pressure regulating valve 15, in such a manner that the pressure on the side of the back pressure regulating valve 15 close to each of the purifying device 13 and the heat exchanger 2, that is, the primary side of the back pressure regulating valve 15 is kept at the predetermined pressure. In addition, the detector 9 is connected to a controller (not shown) for controlling the opening and closing of the predetermined valve 20, the tank 12, and the tank 14 in accordance with the result of the detection by the detector 9.

Figure 2:
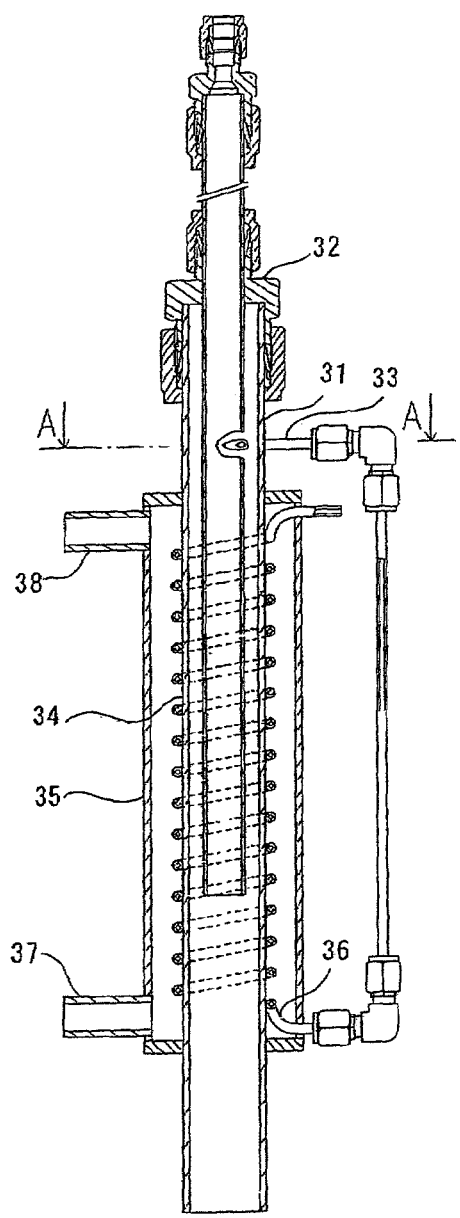
[FIG. 2] A sectional view showing the vertical section of a main portion of an example of a vapor liquid separator of the present invention.
Figure 3:
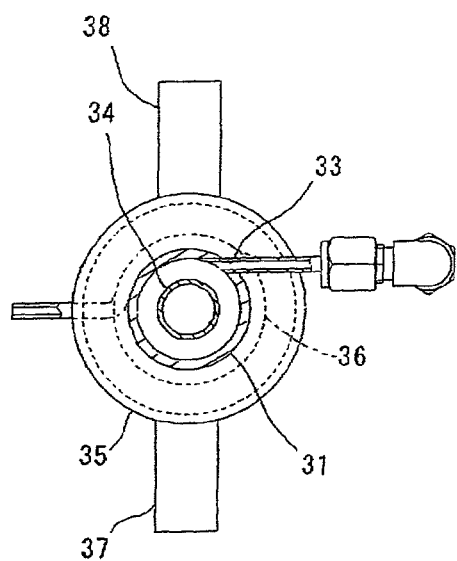
[FIG. 3] A sectional view showing the cross section of a main portion of the vapor liquid separator shown in FIG. 2 taken along the line A-A.

As shown in each of FIGS. 2 and 3, each of the vapor liquid separators 11 has: a cylindrical external cylinder 31 having ends both of which being opened; a flange portion 32 for clogging an opening at one end of the external cylinder 31; an introduction portion 33 as a pipe which is provided along the tangent of the inner peripheral surface in the cross sectional shape of the external cylinder 31 and which is opened in the external cylinder 31; an internal cylinder 34 having ends both of which being opened and which penetrates through the flange portion 32 to extend closer to the other end side of the external cylinder 31 than the introduction portion 33; a jacket 35 that covers the outer peripheral wall surface of the external cylinder 31 for forming a circulating path for a heat medium; and a mobile phase supply pipe 36 that passes the inside of the jacket 35 to be connected to the introduction portion 33.

The jacket 35 is provided with a discharge orifice 38 for the heat medium on one end side of the jacket 35, and is provided with a supply orifice 37 for the heat medium on the other end side of the jacket 35. The mobile phase supply pipe 36 is passed from one end portion of the jacket 35 through the inside of the jacket 35, wound on the outer periphery of the external cylinder 31 from the one end side of the jacket 35 to the other end side of the jacket 35 in a spiral fashion, and taken to the outside from the other end side of the jacket 35 to be connected to the introduction portion 33. The mobile phase supply pipe 36 is connected to the valve 20. The internal cylinder 34 is connected to the purifying device 13. The other end of the external cylinder 31 is connected to the tank 12. The supply orifice 37 and the discharge orifice 38 are connected to heat medium circulating device (not shown).

The purifying device 13 has the same constitution as that of each of the vapor liquid separators 11 shown in each of FIGS.

2 and 3. In the purifying device 13, the mobile phase supply pipe 36 is connected to each of the check valves 21. The internal cylinder 34 is connected to the back pressure regulating valve 15. The other end of the external cylinder 31 is connected to the tank 14. The supply orifice 37 and the discharge orifice 38 are connected to heat medium circulating device (not shown) as in the case of each of the vapor liquid separators 11.

A heat medium circulates through the jackets 35 of the vapor liquid separators 11 and the purifying device 13, whereby the temperature of each external cylinder 31 is regulated to a predetermined temperature.

In addition to those components described above, valves such as a valve, a check valve, and a safety valve, various detecting device such as a pressure gauge, a thermometer, and a flow meter, and peripheral devices such as a heater, a brine chiller, and an accumulator are provided for appropriate sites of the supercritical fluid chromatographic fractionation apparatus although they are not shown.

In this embodiment, the pressure regulating valve 16 is regulated so that carbon dioxide is supplied from the bomb 1 to the heat exchanger 2 at a predetermined pressure (for example, 4 MPa). Carbon dioxide is cooled and liquefied in the heat exchanger 2.

The liquefied gas of carbon dioxide formed in the heat exchanger 2 is stored in the buffer tank 18, and is supplied to the heat exchanger 6 by the pump 3. The liquefied gas supplied to the heat exchanger 6 is supplied with an organic solvent such as a lower alcohol delivered from the solvent tank 4 by the pump 5, whereby the liquefied gas and the organic solvent are mixed. The mixed solvent is supplied to the heat exchanger 6. In the heat exchanger 6, the mixed solvent is heated so that the liquefied gas in the mixed solvent is turned into a supercritical fluid. In addition, the temperature of a mobile phase obtained by mixing the supercritical fluid and the solvent is regulated to the temperature of the column 8 set by the column oven 19 (for example, 40° C.). A solution of a separation object is injected as a sample from the injector 7 into the mobile phase of which the temperature has been regulated.

The sample injected from the injector 7 is sent to the column 8, and various substances in the sample are divided in association with their passage through the column 8.

The substances in the mobile phase that has passed the column 8 are detected by the detector 9. The predetermined valve 20 is opened and the other valves 20 are closed in accordance with the result of the detection by the detector 9. The mobile phase that has passed the detector 9 is sent to the back pressure regulating valve 10. The passing of the mobile phase through the back pressure regulating valve 10 reduces the pressure of the mobile phase, and the mobile phase is supplied through the predetermined valve 20 to the mobile phase supply pipe 36 of the predetermined vapor liquid separator 11.

In the vapor liquid separator 11, the mobile phase supplied to the mobile phase supply pipe 36 moves in the jacket 35 along the outer peripheral surface of the external cylinder 31 in a spiral fashion before it is supplied to the introduction portion 33. Thus, the temperature of the mobile phase is preliminarily regulated to the temperature of the external cylinder 31 before the mobile phase is supplied to the introduction portion 33. The mobile phase of which the temperature has been regulated is introduced from the introduction portion 33 to the external cylinder 31. The mobile phase falls while causing a circular motion along the circumferential direction of the inner peripheral wall surface of the external cylinder 31.

In this process, most of carbon dioxide in the mobile phase is divided as a gas from the mobile phase. The gas divided from the mobile phase passes the internal cylinder 34 to be discharged from the vapor liquid separator 11. The solvent remaining as a result of the division of the gas contains a predetermined substance separated from the sample in the column 8. The solvent falls along the inner peripheral wall surface of the external cylinder 31 to be stored in the tank 12. The substance in the solvent stored in the tank 12 is brought into a concentrated state when the pressure of the system containing the solvent is released because liquefied carbon dioxide is released from the solvent so that the solubility of the substance in the solvent reduces. After the pressure release, a known method such as vacuum concentration is adopted as required so that the substance is precipitated out of the solvent, or the solvent is volatilized. Thus, the substance is taken from the solvent.

In the external cylinder 31, a droplet of the mobile phase generates upon introduction of the mobile phase into the external cylinder 31 with strong momentum or during the flow of the mobile phase in the external cylinder 31 as described above. The internal cylinder 34 extends closer to the other end side (lower side in the vapor liquid separator 11 of FIG. 2) of the external cylinder 31 than the introduction portion 33. Accordingly, the droplet is absorbed by the solvent again, or falls as it is along the external cylinder 31, so it hardly enters the internal cylinder 34. Therefore, a gas mixed with a small amount of the droplet is recovered from the internal cylinder 34.

In the purifying device 13, the gas recovered from the internal cylinder 34 passes from the mobile phase supply pipe 34 to the introduction portion 33 to be introduced into the external cylinder 31. Then, the gas passes the internal cylinder to be discharged from the purifying device 13. The purifying device 13 removes a trace amount of a solvent mixed into the gas owing to the droplet from the gas.

The back pressure regulating valve 15 keeps the pressure on the primary side of the back pressure regulating valve 15 at a predetermined pressure higher than the pressure set by the pressure regulating valve 16. Therefore, the gas discharged from the purifying device 13 is supplied to the heat exchanger 2 so long as the pressure of the gas is equal to or higher than the predetermined pressure. At this time, higher priority is placed on the supply of the gas purified by the purifying device 13 to the heat exchanger 2 than on the supply of the gas from the bomb 1 to the heat exchanger 2. Therefore, the gas purified by the purifying device 13 is preferentially used as a liquefied gas. It should be noted that the flow of the gas purified by the purifying device 13 to the bomb 1 is prevented by the check valve 17.

When the pressure of the gas discharged from the purifying device 13 is lower than the pressure set by the pressure regulating valve 16, carbon dioxide is supplied from the bomb 1 to the heat exchanger 2. The flow of the gas from the bomb 1 to the purifying device 13 is prevented by the back pressure regulating valve 15.

Meanwhile, the back pressure regulating valve 15 supplies an excessive gas for keeping the predetermined pressure to the pipe for discharging. The gas is discharged to outside air directly or after having been subjected to an appropriate treatment. Alternatively, the gas may be compressed by a compressor or the like to be stored in a bomb and recycled.

After that, each of the valves 20 is appropriately opened and closed in accordance with the substance detected by the detector 9, and a desired substance in the sample is taken out.

In this embodiment, the recovery rate of carbon dioxide supplied for use in a supercritical fluid is theoretically about 80% when methanol is used as an organic solvent. Unrecovered carbon dioxide (that is, 20%) is considered to be mainly a portion redissolved into the organic solvent in each of the vapor liquid separators 11.

In addition, in this embodiment, the use of a supercritical fluid of carbon dioxide enables the separation of an acidic substance such as an organic carboxylic acid as it is with neither addition of an acid to the mobile phase nor esterification of the acidic substance. This is probably because carbon dioxide in the mobile phase shows weak acid. The decomposition of the acidic substance as the desired substance can be suppressed because there is no need for adding an acid to the mobile phase. In addition, the recovery rate of the acidic substance from the sample can be increased to be higher than that in the case where the acidic substance is esterified before it is separated because there is no need for esterification.

In addition, in this embodiment, the use of a column having an optical resolution ability enables separation of an optical isomer at high purity. For example, in the case of the optical resolution of the racemic body of guaifenesin using a CHIRALCEL OD (1 cmΦ×25 cmL) manufactured by DAICEL CHEMICAL INDUSTRIES, LTD. as the column, an R body having an optical purity of 99.0% can be obtained in a yield of 94.9%, and an S body having an optical purity of 98.8% can be obtained in a yield of 98.8%.

In addition, in this embodiment, the intermittent injection of the sample into the mobile phase enables the separation of the desired substance in the sample with high productivity. For example, in the case of the above-mentioned optical resolution, 4.06 kg of the optical isomer can be produced per day by using 1 kg of a filler for the column.

In this embodiment, after the liquefied gas has been mixed with the solvent, the temperature of the mixed solvent is regulated, and the liquefied gas in the mixed solvent is turned into the supercritical fluid. Alternatively, for example, the following procedure may be adopted: a heat exchanger, which heats the liquefied gas before being mixed with the solvent in such a manner that the temperature of the liquefied gas exceeds a critical temperature, is further provided to form the supercritical fluid, the supercritical fluid is mixed with the solvent to form a mobile phase, and the temperature of the mobile phase is regulated to a temperature suitable for separation by the column 8.

In addition, in this embodiment, each of the vapor liquid separators 11 is installed to divide the gas upward, and the solvent downward. However, the present invention is not limited to such installation. Alternatively, the vapor liquid separators 11 and the purifying device 13 may be installed obliquely or orthogonally to a vertical direction.

In addition, in this embodiment, each of the vapor liquid separators 11 is provided with the single tank 12. However, the number of the tanks 12 is not particularly limited in the present invention. For example, the following procedure can be adopted: each of the vapor liquid separators 11 is provided with multiple tanks connected in series, decompression is performed between the tanks at any time, and the redissolution of a gas into the solvent is suppressed. For example, recovering carbon dioxide dissolved into the solvent collected by the tank 12 below each of the vapor liquid separators 11 requires recovering carbon dioxide by using any one of second and subsequent tanks to be further connected to the tank 12. In such a case, the pressure of each of the second and subsequent tanks is further reduced (for example, 1 MPa). Carbon dioxide released from the solvent in any one of the second and subsequent tanks can be compressed and liquefied by using a compressor, and can be sent to the buffer tank 18.

In this embodiment, the mobile phase containing the desired substance in the sample is subjected to vapor liquid separation. Accordingly, the solvent as the divided liquid contains the desired substance, and the desired substance in a concentrated state can be easily recovered only by releasing the divided solvent from a pressure. In addition, the desired substance in the concentrated state can be recovered only by releasing the solvent from a pressure, so this embodiment is advantageous also for the separation of a substance unstable in heat that is apt to change with time owing to heat.

In addition, in this embodiment, the gas obtained by subjecting the mobile phase to vapor liquid separation is supplied to the heat exchanger 2 against the pressure of the gas from the bomb 1, whereby the liquefied gas is formed. Accordingly, carbon dioxide from which the supercritical fluid is formed can be recycled in supercritical fluid chromatography using a mixed solvent of the supercritical fluid of carbon dioxide and an organic solvent as a mobile phase. As a result, a cost for carbon dioxide can be reduced. In addition, the discharge of carbon dioxide to an environment in supercritical fluid chromatography can be suppressed.

In addition, in this embodiment, the vapor liquid separators 11 each provided with the internal cylinder 34 extending in the external cylinder 31 up to the position at which no droplet of the mobile phase generates in the external cylinder 31 are used. Accordingly, mixing with a droplet of the mobile phase that generates upon vapor liquid separation can be reduced, and a gas having a high purity that can be recycled as the mobile phase for new chromatography can be obtained by means of vapor liquid separation.

In addition, in this embodiment, the mobile phase before being introduced into the external cylinder 31 is passed through the inside of the jacket 35 for regulating the temperature of the external cylinder 31. Accordingly, the temperature of the mobile phase before being introduced into the external cylinder 31 can be regulated to the temperature of the external cylinder 31 in advance. Therefore, efficiency of vapor liquid separation increased by regulating the temperature of the external cylinder 31 can be further enhanced.

In addition, in this embodiment, the mobile phase supply pipe 36 is wound on the outer peripheral wall surface of the external cylinder 31 in the jacket 35. Accordingly, the efficiency of vapor liquid separation increased by regulating the temperature of the external cylinder 31 can be further increased by using a compact constitution.

In addition, in this embodiment, the external cylinder 31 is of a cylindrical shape, so a pressure is uniformly applied to the peripheral wall of the external cylinder 31. Accordingly, the durability of each of the vapor liquid separators 11 in vapor liquid separation under a high-pressure condition such as supercritical fluid chromatography can be further improved.

In addition, in this embodiment, the purifying device 13 is provided, so a trace of an impurity such as the solvent in the gas divided by each of the vapor liquid separators 11 is further removed. As a result, a gas with an improved purity can be recovered, and can be recycled as the mobile phase.

In addition, in this embodiment, the check valve 17 for preventing the flow of a gas from the heat exchanger 2 to the bomb 1 is provided between the bomb 1 and the heat exchanger 2, so the gas purified by the purifying device 13 can be prevented from flowing into the bomb 1.

In addition, in this embodiment, the check valve 21 for preventing the flow of a gas from the purifying device 13 to each of the vapor liquid separators 11 is provided between each of the vapor liquid separators 11 and the purifying device 13 in correspondence with each of the vapor liquid separators 11. Accordingly, the back flow of a gas from the purifying device 13 to the external cylinder 31 or the inflow of a gas from one of the vapor liquid separators 11 to any one of the other vapor liquid separators 11 can be prevented.

Industrial Applicability

According to the present invention, in a method of separating a substance by supercritical fluid chromatography using a mobile phase comprising a supercritical fluid formed from a liquefied gas obtained by liquefying a gas and a solvent, the mobile phase that has passed a column is subjected to vapor liquid separation, and, when the pressure of the gas divided from the mobile phase is higher than the pressure of a gas supplied for the formation of the liquefied gas from gas supply device, the gas divided from the mobile phase is liquefied. Accordingly, a gas from which a supercritical fluid is formed can be recycled in a method of separating a substance by supercritical fluid chromatography using a mobile phase comprising the supercritical fluid and a solvent.

In the present invention, the use of a vapor liquid separator comprising an external cylinder having ends both of which being opened, a flange portion for clogging an opening at one end of the external cylinder, an introduction portion for introducing a mobile phase into the external cylinder in a circumferential direction along the inner peripheral wall surface of the external cylinder, and an internal cylinder having ends both of which being opened and which penetrates through the flange portion to extend closer to the other end side of the external cylinder than the introduction portion in the step of dividing the mobile phase into a solvent and a gas, is further effective in improving the durability of the vapor liquid separator and performing vapor liquid separation with high efficiency in supercritical fluid chromatography under a high-pressure condition.

In the present invention, further providing the vapor liquid separator with a jacket that covers the outer peripheral wall surface of the external cylinder for regulating the temperature of the external cylinder and a mobile phase supply pipe that passes the inside of the jacket to be connected to the introduction portion for supplying the mobile phase to the introduction portion is further effective in further improving the efficiency of vapor liquid separation in supercritical fluid chromatography.

In the present invention, using a sample which comprises a mixture of optical isomers and of which the desired substance is one of the optical isomers is further effective in efficiently fractionating an optical isomer with further suppressed mixing with an impurity and having a high purity.

In addition, the vapor liquid separator of the present invention has the above-described constitution, so it can be widely used in a separation of a gas with further suppressed mixing with an impurity and having a high purity, and in vapor liquid separation in the technical field where such gas is recycled.

In addition, further providing the vapor liquid separator of the present invention with the jacket and the mobile phase supply pipe is further effective in improving separation efficiency in vapor liquid separation.

The invention claimed is:

1. A vapor liquid separator for use in a method of separating a substance by supercritical fluid chromatography of injecting a sample comprising a desired substance into a mobile phase comprising a supercritical fluid and a solvent, passing the sample through a column for separating the desired substance from the sample to separate the desired substance in the sample, dividing the mobile phase that has been passed through the column into the solvent and a gas, and separating the desired substance from the solvent, wherein the vapor liquid separator comprises:
   an external cylinder having ends both of which being opened;
   a flange portion for clogging an opening at one end of the external cylinder;
   an introduction portion for introducing the mobile phase into the external cylinder in a circumferential direction along an inner peripheral wall surface of the external cylinder; and
   an internal cylinder having ends both of which being opened and which penetrates through the flange portion to extend closer to an other end side of the external cylinder than the introduction portion.

2. The vapor liquid separator according to claim 1, further comprising:
   a jacket that covers an outer peripheral wall surface of the external cylinder for regulating a temperature of the external cylinder; and
   a mobile phase supply pipe that passes an inside of the jacket to be connected to the introduction portion for supplying the mobile phase to the introduction portion.

3. The vapor liquid separator according to claim 1, wherein:
   the sample comprises a mixture of optical isomers; and
   the desired substance comprises one of the optical isomers.

4. The vapor liquid separator according to claim 2, wherein:
   the sample comprises a mixture of optical isomers; and
   the desired substance comprises one of the optical isomers.

* * * * *